United States Patent [19]

Evans et al.

[11] 4,366,163
[45] * Dec. 28, 1982

[54] ANTI-HYPERTENSIVE CHROMANOL DERIVATIVES

[75] Inventors: John M. Evans, Roydon; Graham A. Showell; Charles S. Fake, both of Harlow, all of England

[73] Assignee: Beecham Group Limited, England

[*] Notice: The portion of the term of this patent subsequent to Dec. 14, 1999, has been disclaimed.

[21] Appl. No.: 186,709

[22] Filed: Sep. 12, 1980

[30] Foreign Application Priority Data

Sep. 28, 1979 [GB] United Kingdom ............ 7933721
May 3, 1980 [GB] United Kingdom ............ 8014932

[51] Int. Cl.³ ............... A61K 31/445; C07D 405/04
[52] U.S. Cl. .................. 424/267; 424/246; 424/248.54; 424/248.55; 424/248.56; 424/248.57; 424/248.58; 424/270; 424/272; 424/274; 424/283; 544/58.7; 544/62; 544/151; 546/196; 548/146; 548/214; 548/215; 548/240; 548/525; 549/399
[58] Field of Search ............ 260/345.2, 345.5, 326.34, 260/326.5 CA; 546/196; 548/146, 214, 215, 240, 151, 58.7, 62; 424/267, 274, 270, 272, 283, 248.54, 248.55, 248.56, 248.57, 248.58, 246

[56] References Cited

U.S. PATENT DOCUMENTS 4,048,317 9/1977 Watts .................. 546/196 X
4,251,537 2/1981 Evans ................... 546/196 X

FOREIGN PATENT DOCUMENTS 2713670 10/1977 Fed. Rep. of Germany .
1548221 7/1979 United Kingdom .

Primary Examiner—Richard A. Schwartz
Attorney, Agent, or Firm—Jacobs & Jacobs

[57] ABSTRACT

Compounds of the formula (I)

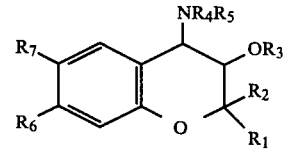

and salts and pro-drugs thereof, wherein:
$R_1$ is a hydrogen atom or a lower alkyl group;
$R_2$ is a hydrogen atom or a lower alkyl group;
$R_3$ is a hydrogen atom or a lower alkyl group;
$R_4$ is a hydrogen atom or an alkyl group;
$R_5$ is a lower alkyl or a substituted alkyl group;
or $R_4$ and $R_5$ are joined so that together with the nitrogen atom to which they are attached they form a 5-, 6- or 7-membered ring optionally containing an oxygen or sulphur atom;
$R_6$ is an electron donating group;
$R_7$ is an electron withdrawing group; and
the $NR_4R_5$ and $OR_3$ moieties are trans having compositions containing them and processes for their preparation.

10 Claims, No Drawings

ANTI-HYPERTENSIVE CHROMANOL DERIVATIVES

This invention relates to chromanol derivatives, a process for their preparation, and to their use.

U.K. Pat. Nos 1,495,526 and 1,511,187 disclose that derivatives of trans-3-hydroxy-4-aminochroman have blood pressure lowering activity.

A group of compounds have now been found that also possess good blood pressure lowering activity, with low levels of unwanted cardiac effects.

Accordingly, the present invention provides the compounds of the formula (I):

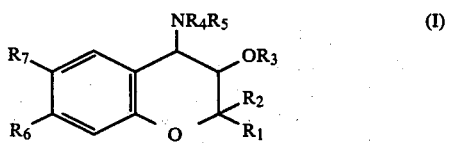

and salts and pro-drugs thereof, wherein:
- $R_1$ is a hydrogen atom or a lower alkyl group;
- $R_2$ is a hydrogen atom or a lower alkyl group;
- $R_3$ is a hydrogen atom or a lower alkyl group;
- $R_4$ is a hydrogen atom or an alkyl group;
- $R_5$ is a lower alkyl or a substituted alkyl group;
- or $R_4$ and $R_5$ are joined so that together with the nitrogen atom to which they are attached they form a 5-, 6- or 7-membered ring optionally containing an oxygen or sulphur atom;
- $R_6$ is an electron donating group;
- $R_7$ is an electron withdrawing group; and the $NR_4R_5$ and $OR_3$ moieties are trans.

The terms 'electron withdrawing group' and 'electron donating group' are terms well recognised in the art. Such groups are readily identifiable by the skilled man. Standard references to such terms include Finar 'Organic Chemistry' Vol. 1, pp 21, 22.

When used herein the term "alkyl" means an alkyl group of up to 5 carbon atoms; the term "lower" means a group of up to 3 carbon atoms; and term "substituted alkyl" means a straight chain alkyl group of at least 3 carbon atoms terminally substituted by a chlorine atom.

Suitably $R_1$ is a hydrogen atom or a methyl or ethyl group. Most suitably $R_1$ is a methyl group.

Suitably $R_2$ is a hydrogen atom or a methyl or ethyl group. Most suitably $R_2$ is a methyl group.

Apt values for $R_3$ include the hydrogen atom and the methyl and ethyl groups. Particularly apt values for $R_3$ include the hydrogen atom and the methyl group. A favoured value for $R_3$ is the hydrogen atom.

Suitable acyclic values for the $NR_4R_5$ moiety include those wherein $R_4$ is a hydrogen atom or methyl group and $R_5$ is an alkyl group. Specific values for acyclic $NR_4R_5$ moieties include dimethylamino, isopropylamino and t-butylamino.

Suitable cyclic values for the $NR_4R_5$ moiety include those of the sub-formula (a):

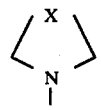

wherein X is a bond, a methylene group, an ethylene group, an ethylidene group, an oxygen, or a sulphur atom. Most suitably X is a bond or a methylene group.

Suitable electron donating groups $R_6$ include the amino, lower acylamino, lower alkylamino, lower dialkylamino, hydroxyl, lower alkoxyl and lower alkyl groups. Apt groups $R_6$ thus include the $NH_2$, $NH.CO.CH_3$, $OCH_3$, $OH$ and $CH_3$ groups. Favoured groups $R_6$ include the $NH_2$, $NH.CO.CH_3$, $OCH_3$ and $OH$ groups of which the $NH_2$ and $NH.CO.CH_3$ are particularly favoured.

Suitable electron withdrawing groups $R_7$ include the nitro, cyano, carboxamido, acetyl and lower alkoxycarbonyl groups. Favoured groups $R_7$ include the nitro, cyano, carboxamido and acetyl groups. Particularly favoured $R_7$ groups are the nitro and cyano groups.

Suitable pro-drugs of the compounds of the formula (I) include esters of those compounds wherein $R_3$ is a hydrogen atom. Suitable esters include those of fatty acids up to 18 carbon atoms mores suitably, those of up to 4 carbon atoms. Examples of such esters include those of acetic, propionic, butyric, oleic, palmitic, stearic, benzoic, pivalic and the like acids.

Suitable salts of the compounds of this invention include acid addition salts with pharmaceutically acceptable inorganic or organic acids such as hydrochloric, hydrobromic, phosphoric, sulphuric, toluene sulphonic, methane sulphonic, acetic, propionic, succinic, citric, lactic, tartaric, maleic, mandelic or like acid.

Favoured compounds of this invention include those of the formula (II):

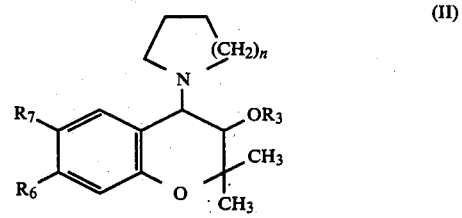

and salts and pro-drugs thereof wherein $R_3$, $R_6$ and $R_7$ have the values herein before indicated and n is 1 or 2, the cyclic amino and $OR_3$ moieties being trans.

Suitable and particularly favoured groups $R_6$ and $R_7$ are as hereinbefore described in relation to formula (I).

From the foregoing it will be realised that certain preferred compounds of this invention are those of the formulae (III) and (IV):

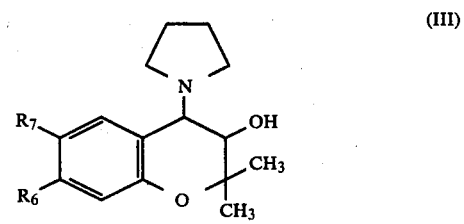

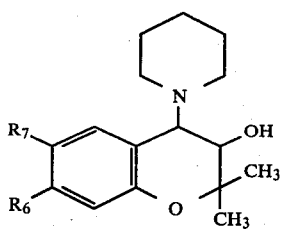

(IV)

and salts thereof wherein $R_6$ and $R_7$ are as hereinbefore indicated, the cyclic amino and hydroxy moieties being trans.

Suitable and particularly favoured groups $R_6$ and $R_7$ are as hereinbefore described in relation to formula (I).

Other classes of compounds of particular note are those of the formula (V):

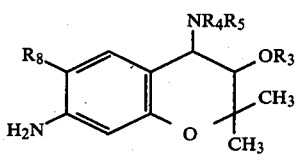

(V)

and salts and pro-drugs therefore wherein $R_3$, $R_4$ and $R_5$ are as hereinbefore indicated, the $NR_4R_5$ and $OR_3$ moieties are trans, and $R_8$ is nitro or cyano.

The compounds of the invention exist in optically active forms. Those skilled in the chemical arts will realise that racemic mixtures of amino compounds can be separated into pure optical isomers using such techniques as fractional crystallisation using optically active acids or the like.

The present invention also provides a process for the preparation of a compound of the formula (I) which comprises the reaction of a compound of the formula (VI):

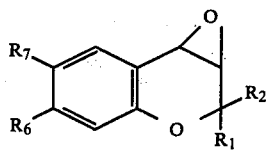

(VI)

wherein $R_1$, $R_2$, $R_6$ and $R_7$ are as defined in relation to formula (I) with the proviso that any amino group present in $R_6$ or $R_7$ is masked; with a compound of the formula (VII):

$HNR_4R_5$ (VII)

wherein $R_4$ and $R_5$ are as defined in relation to formula (I); and thereafter if desired or necessary converting $R_3$, $R_6$ or $R_7$ in the thus formed compound to another group $R_3$, $R_6$ or $R_7$, removing the "masking" from any amino group present in $R_6$ or $R_7$, or forming a salt of the compound.

The reaction with the epoxide may be carried out at any non-extreme low, medium or high temperature (for example, $-10°$ C. to $200°$ C.) but in general ambient or slightly elevated temperatures are most suitable (for example $12°$ C. to $100°$ C.). The reaction is normally carried out in a solvent such as an alcohol or ketone, for example methanol, ethanol, propanol, acetone or methylethylketone.

It has been found that the reaction proceeds smoothly if carried out in refluxing ethanol.

The above reaction gives a trans product substantially free of the cis-isomer.

The desired product may be obtained from the reaction mixture by removal of the solvent which is normally accomplished by evaporation under reduced pressure. The initial product may contain some epoxide. This may be separated by dissolving the reaction product in ethyl acetate and extracting into dilute acid. If desired the solvent may be evaporated at this stage but it is usually more convenient to neutralise, back extract into ethyl acetate and recover by evaporation at reduced pressure.

The groups $R_3$, $R_6$ and $R_7$ may be interconverted in the usual way. For example a $R_3$ hydrogen can be methylated, ethylated or propylated, and a $R_7$ cyano can be converted to a $R_7$ carboxamido by treatment with acid.

The term "masking" herein means reversibly protecting in a manner wich temporarily renders the amino group non-basic. Suitable methods of masking include acylation. The acylamino group may be converted to the amino group by such conventional processes as hydrolysis after the addition reaction has been effected.

If it is desired to deprotect a protected amino group in the presence of a cyano group then a more suitable method is to use a trifluoroacetyl protecting group which may be removed by mild hydrolysis. A further suitable method of deprotection of a protected amino group in the presence of a cyano group is to utilise a benzyloxycarbonyl or p-nitrobenzyloxycarbonyl protecting group which groups may be removed by mild catalytic hydrogenolysis. Benzyloxycarbonyl amino and p-nitrobenzyloxycarbonylamino groups may be formed by reaction of the appropriate chloride with the free amine function.

If a salt is desired this may be prepared from the free base in the usual way, for example the free base may be dissolved in diethyl ether containing a little ethanol and treated with a solution of the acid for example in diethyl ether. The desired salt may then be collected by filtration.

Etherification of the initially produced compound of the formula (I) wherein $R_3$ is a hydrogen atom may be effected in conventional manner such as reaction with an alkyl iodide in the presence of a base such as potassium t-butoxide in an inert solvent such as toluene. If required, $R_6$ may be suitably protected during this etherification reaction and subsequently deprotected.

Preparation of esters of the compounds of formula (I) wherein $R_3$ is hydrogen may be by such conventional methods of esterification as reaction with an acylating agent optionally in the presence of an acid acceptor. Suitable acylating agents include acid halides such as bromides, chlorides and anhydrides.

Esters of the compound of the formula (I) wherein $R_3$ is hydrogen also may be prepared by reaction with an acid in the presence of a condensation promoting agent such as dicyclohexylcarbodiimide or its chemical equivalent. Such reactions are generally carried out in a non-hydroxylic solvent at a non-extreme temperature. If required, $R_6$ can be suitably masked during this acylation step and then deprotected.

The epoxides of the formula (VI) may be isolated or used in situ and may be prepared according to the following reaction sequence.

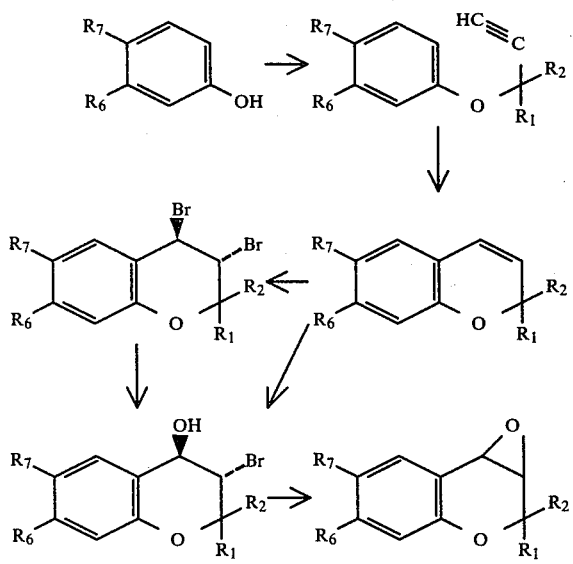

This reaction sequence may be brought about under conditions analogous to those described in the aforementioned U.K. Patents.

The above reaction sequence can produce mixtures of compounds owing to the two methods of ring closure of the propargyl ether. It is thus useful to separate any undesired isomer of the chromene before proceeding, for example chromatographically. Also a monofunctional chromene may be converted to a difunctional one by chemical manipulation in known manner, for example a nitro group may be introduced next to an acetamido group.

In a further aspect the product invention also provides a pharmaceutical composition which comprises a compound of this invention and a pharmaceutically acceptable carrier.

The compositions of this invention are most suitably adapted for oral administration although adaption for other modes of administration for example by injection are also possible.

In order to obtain consistency of administration it is preferred that the compositions of this invention are in the form of a unit dose. Suitable unit dose forms include tablets, capsules, ampoules and powders in sachets. Such unit dose forms aptly contain from 1 to 100 mg of the compound of this invention and more usually from 2 to 75 mg, for example 5 to 50 mg. Such compositions may be administered from 1 to 6 times a day, more usually from 2 to 4 times a day, in a manner such that the daily dose is from 5 to 200 mg for a 70 kg human adult and more aptly from 10 to 100 mg.

Shaped compositions are favoured composition aspects.

The compositions of this invention may be formulated in conventional manner, for example in a manner similar to that used for known antihypertensive agents such as hydrallazine.

In addition such compositions may contain further active agents such as other antihypertensive agents especially $\beta$-blocking agents, and diuretics.

The following Examples illustrate the invention.

EXAMPLE 1

7-Acetamido-3,4-dihydro-2,2-dimethyl-6-nitro-trans-4-piperidino-2H-benzo[b]pyran-3-ol methane sulphonate 2,2-Dimethyl-7-nitro-2H-benzo[b]pyran (40.00 g, the preparation of which was disclosed in U.K. Pat. No. 1,548,222), glacial acetic acid (200 ml), acetic anhydride (120 ml) and electrolytic iron powder (88 g) were stirred and heated at 120° C. for 16 hours. Dilution with water, extraction via chloroform, followed by washing of the organic layer with water and sodium bicarbonate solution, drying evaporation etc., gave a crude gum which was chromatographed on a silica gel column using ethyl acetate—60°--80° petroleum ether mixtures in a gradient elution technique. Fractions homogeneous by TLC were combined and recrystallised from 60°-80° petroleum ether to give 7-acetamido-2,2-dimethyl-2H-benzo[b]pyran (5.27 g) as white needles of mp 80°-81° C.; nmr (CDCl$_3$) δ 1.39 (6H), 2.12 (3H), 5.48 (1H, d, J=10), 6.21 (1H, d, J=10), 6.76-7.34 (3H, m), 8.95 (1H). Anal. Calcd for C$_{13}$H$_{15}$NO$_2$: C, 71.87; H, 6.96; N, 6.45. Found: C, 72.00; H, 7.11; N, 6.23%.

To this acetamidobenzopyran (5.17 g) dissolved in glacial acetic acid (29 ml) was added fuming nitric acid (1.70 ml) dropwise with stirring at 0° C. Dilution with water and extraction via ethyl acetate gave a yellow solid (6.63 g) which was chromatographed on a silica gel column using ethyl acetate—60°-80° petroleum ether mixtures in a gradient elution technique. The least polar component was recrystallised as yellow needles of 7-acetamido-2,2-dimethyl-6-nitro-2H-benzol[b]pyran (1.80 g) of mp 148°-150° C. from ethanol; nmr (CDCl$_3$) δ 1.47 (6H), 2.28 (3H), 5.72 (1H, d, J=10), 6.33 (1H, d, J=10), 7.93 (1H), 8.25 (1H). Anal. Calcd for C$_{13}$H$_{14}$N$_2$O$_4$: C, 59.54; H, 5.38; N, 10.69. Found: C, 59.61; H, 5.41; N, 10.69%.

To this nitro compound (1.80 g) dissolved in dimethyl sulphoxide (25 ml) and water (0.25 ml) was added N-bromo-succinimide (2.47 g) in one portion and with vigorous stirring. After dilution with water, extraction via ethyl acetate gave a yellow solid (2.59 g). A small portion recrystallised from ethanol gave 7-acetamido-trans-3-bromo-3,4-dihydro-2,2-dimethyl-6-nitro-2H-benzo[b]pyran-4-ol as yellow needles mp 205°-206°; n.m.r. (CDCl$_3$) δ 1.45 (3H), 1;63 (3H), 2.25 (3H), 4.07 (1H, d, J=9), 4.78 (1H, d, J=9), 8.08 (1H), 8.41 (1H), 10.31 (1H). Anal. Calcd for C$_{13}$H$_{15}$BrN$_2$O$_5$: C, 43.45; H, 4.18; N, 7.80; Br, 22.28. Found C, 43.99; H, 4.39; N, 8.35; Br 22.02%.

This bromohydrin (2.50 g), sodium hydroxide pellets (4.00 g), water (20 ml) and dioxan (100 ml) were stirred at room temperature for 40 min. Dilution with water (1 liter) and extraction via ethyl acetate gave a crude yellow solid (2.00 g) which was refluxed with piperidine (2 ml) in ethanol (100 ml) for 26 hours. Evaporation of solvents, taking up the residue in ethyl acetate, washing with water, and acid-base manipulation gave the crude free base (0.56 g). Treatment of this free base (0.28 g) with methane sulphonic acid (0.052 ml) in the minimum volume of ethanol-diethyl ethyl gave a yellow precipitate. Three recrystallisations from ethanol-diethyl ether gave 7-acetamido-3,4-dihydro-2,2-dimethyl-6-nitro-trans-4-piperidino-2H-benzo[b]pyran-3-ol methane sulphonate as a yellow powder (0.05 g) mp 177°-181° C.; nmr (DMSOd$_6$) δ 1.09 (3H), 1.48 (3H), 1.67 (6H, broad m), 2.13 (3H), 2.40 (3H), 3.50 (4H, broad m) and 4.23, 4.71 (each 1H, d, J=9) overlapped with 3.03–4.94 (3H-very broad m), 7.52 (1H), 8.71 (1H).

Anal. Calcd for $C_{19}H_{29}N_3O_8S$: C, 49.66; H, 6.36; N, 9.15. Found: C, 49.66; H, 6.59 N, 9.21%.

EXAMPLE 2

7-Amino-3,4-dihydro-2,2-dimethyl-6-nitro-trans-4-piperidino-2H-benzo[b]pyran-3-ol methane sulphonate The crude free base obtained in example 1 (0.21 g), 5 N hydrochloric acid (2 ml) and ethanol (5 ml) were heated on a water bath for 3 hours. Dilution with water (100 ml) and basification with 10% sodium hydroxide solution, followed by extraction with ethyl acetate, washing and drying etc., gave a reddish-yellow gum (0.22 g) which was treated with methane sulphonic acid (0.035 ml) in the minimum volume of ethanol. Addition of diethyl ether gave 7-amino-3,4-dihydro-2,2-dimethyl-6-nitro-trans-4-piperidino-2H-benzo[b]pyran-3-ol methane sulphonate as the monohydrate mp 179°–182°; nmr (DMSOd$_6$) δ 1.07 (3H), 1.45 (3H), 1.65 (6H, broad m), 2.38 (3H), 3.44 (8H, m, (4 exchangeable H)), 4.15 (1H, d, J=8), 4.55 (1H, d, J=8), 6.40 (1H), 8.60 (1H). Anal. Calcd for $C_{17}H_{29}N_3SO_8$: C, 46.89; H, 6.71; N, 9.65. Found: C, 47.18; H, 6.37; N, 9.25%.

EXAMPLE 3

7-Amino-3,4-dihydro-2,2-dimethyl-6-nitro-trans-4-pyrrolidino-2H-benzo[b]pyran-3-ol methane sulphonate Crude epoxide (0.43 g, obtained from the corresponding bromohydrin as yellow needles in a similar manner to that of Example 1) and pyrrolidine (0.15 ml) were refluxed in ethanol (50 ml) for 3 hours. Evaporation of the solvents gave a brown gum which was refluxed with 5 N HCl (5 ml) and ethanol (10 ml) for a total of 6 hours. The reaction mixture was diluted with water, basified, extracted with ethyl acetate, washed (H$_2$O), dried and evaporated in vacuo to afford a gum which was subjected to an acid/base extraction to give the basic component (0.18 g), nmr (CDCl$_3$) δ 1.17 (s, 3H), 1.41 (s, 3H), 1.62–2.01 (m), 2.46–3.32 (m, 4H), 3.49 (d, J=9, 1H), 3.91 (d, J=9, 1H), 3.43–3.86 (broad m, 1H), 5.77–6.21 (broad m) overlapped with 6.12 (s, total of 2H), 8.05 (s, 1H). The methane sulphonate salt was prepared in a similar manner to that of Example 2 to give 7-amino-3,4-dihydro-2,2-dimethyl-6-nitro-trans-4-pyrrolidino-2H-benzo[b]pyran-3-ol methane sulphonate (0.092 g) mp 193°–195° C. Anal. Calcd. for $C_{16}H_{25}N_3SO_7$: C, 47.63; H, 6.25; N, 10.42. Found: C, 47.73; H, 6.57; N, 9.46. Consistent analysis was not obtained. Mass spectrum: Chemical Ionization, $[M+H-CH_3SO_3H]^+$ at m/e=308.

EXAMPLE 4

6-Acetyl-3,4-dihydro-2,2-dimethyl-7-methoxy-trans-4-pyrrolidino-2H-benzo[b]pyran-3-ol hydrochloride 2,3-Dihydro-2,2-dimethyl-7-hydroxy-4H-benzo[b]pyran-4-one (9.98 g), amalgamated zinc dust (50.0 g), 5 N hydrochloric acid (400 ml) and glacial acetic acid (100 ml) were stirred and refluxed for 4 hours then stirred at room temperature for 18 hours. The reaction mixture was extracted with diethyl ether, washed with water, dried and evaporated in vacuo to afford a dark red oil which was distilled to give 2,3-dihydro-2,2-dimethyl-7-hydroxy-4H-benzo[b]pyran (4.22 g) as an orange oil, bp 138°–146° C. (0.02 mm).

This benzopyran (4.20 g), methyl iodide (5.86 ml) and potassium carbonate (10 g) were refluxed in dry acetone (150 ml) for 3 days. The mixture was cooled, filtered, and the filtrate evaporated to dryness. The resulting residue was dissolved in diethyl ether, washed with water, 10% sodium hydroxide solution and brine, dried and evaporated to dryness in vacuo to give a yellow oil which was purified via a silica gel column using ethyl acetate −60° −80° petroleum ether mixtures in a gradient elution technique to afford 2,3-dihydro-2,2-dimethyl-7-methoxy-4H-benzo[b]pyran (3.10 g) as a yellow oil.

To a cooled mixture of this benzopyran (2.52 g), acetyl chloride (1.07 ml) and carbon disulphide (40 ml) was added powdered aluminum chloride (2.27 g), with stirring over 3 minutes.

The dark red mixture was allowed to warm to room temperature and left for 1 hour. After decanting off the carbon disulphide the residue was treated with ice/dilute hydrochloric acid, and the resulting emulsion was extracted with ethyl acetate, washed with water, brine, dried and evaporated to dryness in vacuo to give a dark yellow oil which was purified via a silica gel column using ethyl acetate −60° −80° petroleum ether in a gradient technique to afford 6-acetyl-2,3-dihydro-2,2-dimethyl-7-methoxy-4H-benzo[b]pyran (0.88 g) as a thick yellow oil, nmr (CDCl$_3$) δ 1.34 (s, 6H), 1.80 (t, slight distortion, J=7), 2.54 (s) overlapped with 2.72 (t, slight distortion, J=7, total of 5H), 3.85 (s, 3H), 6.38 (s, 1H), 7.65 (s, 1H); ir (neat) 1660 cm$^{-1}$.

Anal. Calcd. for $C_{14}H_{18}O_3$: C, 71.77; H, 7.74. Found: C, 70.84; H, 7.92%. Consistent analysis was not obtained. Mass spectrum: m/e=234.

This benzopyran (0.84 g) and 2,3-dichloro-5,6-dicyano-1,4-benzoquinone (0.815 g) were refluxed in dry toluene (40 ml) for 5½ hours, cooled, filtered, and evaporated to dryness in vacuo to give a green gum which was purified via a silica gel column using a 20% ethyl acetate—60°-80° petroleum ether mixture to afford 6-acetyl-2,2-dimethyl-7-methoxy-2H-benzo[b]pyran (0.32 g) as viscous, dark orange oil.

To a stirred solution of this benzopyran (0.32 g) and water (0.025 ml) in dimethyl sulphoxide (20 ml) was added N-bromosuccinimide (0.245 g), and the solution stirred for 30 minutes. The solution was then diluted with water and extracted into ethyl acetate. The organic phase was washed with water, brine, dried and evaporated in vacuo to afford 6-acetyl-trans-3-bromo-3,4-dihydro-2,2-dimethyl-7-methoxy-2H-benzo[b]pyran-4-ol (0.30 g) as a dark yellow/green gum.

This crude bromohydrin (0.29 g) and pyrrolidine (0.29 ml) were refluxed in propan-2-ol (30 ml) for 2 days. After removal of the solvents in vacuo, the residual gum was dissolved in ethyl acetate, washed with 10% sodium carbonate solution, water, and subjected to an acid/base extraction to give the basic material as a brown solid (0.10 g). This free base was dissolved in ethanol and addition of ethereal-HCl followed by evaporation of the solvents gave the crude salt as a brown solid. One recrystallisation from ethanol-ether gave 6-acetyl-3,4-dihydro-2,2-dimethyl-7-methoxy-trans-4-pyrrolidino-2H-benzo[b]pyran-3-ol hydrochloride (0.04 g) as reddish/brown crystals, mp 189°–192° C.; ir (KBr disc) 1615 cm$^{-1}$. Consistent analysis was not obtained. Mass spectrum: initial cleavage of O-C$_2$ and C$_3$-C$_4$ bonds (retro Diels-Alder) gave a peak at m/e=247 in the EI spectrum; $[M=H-HCl]^+$ at m/e=320 in the chemical ionization spectrum.

EXAMPLE 5

7-Acetamido-6-cyano-3,4-dihydro-2,2-dimethyl-trans-4-pyrrolidino-2H-benzo[b]pyran-3-ol To a cooled solution of 6-amino-2,2-dimethyl-7-nitro-2H-benzo[b]pyran (20.00 g, of the preparation of which was disclosed in British Pat. No. 1,548,222) in glacial acetic acid (800 ml) was added concentrated sulphuric acid (400 ml) and the solution stirred at 8° C. Nitrosyl sulphuric acid (prepared by dissolving sodium nitrite (6.62 g) in cold concentrated sulphuric acid (200 ml) the mixture being warmed to dissolve the solid then re-cooled to approximately 4° C.) was added keeping the temperature of the reaction mixture below 12° C. The dark, viscous mixture was stirred at approximately 7° C. for a further hour then poured into a cold (approx. 5° C.) solution of potassium iodide (15.27 g) in water (200 ml). Toluene (800 ml) was added to dissolve the resulting precipitate and the mixture stirred in an ice bath for 20 minutes, then at room temperature for 18 hours. The reaction mixture was diluted with water (500 ml), the organic phase was separated, washed with water, dried and evaporated in vacuo to afford the required 2,2-dimethyl-6-iodo-7-nitro-2H-benzo[b]pyran (11.84 g, 39%) as a red gum; nmr (CDCl$_3$) δ 1.43 (s, 6H), 5.79 (d, J=10, 1H), 6.26 (d, J=10, 1H), 7.28 (s, 1H), 7.51 (s, 1H). This compound was used immediately in the next step. This crude benzopyran (11.74 g), cuprous cyanide (3.20 g) and anhydrous pyridine (450 ml) were heated under reflux for 8 hours. The mixture was concentrated to approximately half volume then diluted with water (1 liter) and the resulting emulsion extracted into ethyl acetate, the organic phase was washed with water, dried and evaporated in vacuo to afford a brown solid (9.62 g) which was purified on a silica gel column using ethyl acetate $-60°$ $-80°$ petroleum ether mixtures by a gradient elution technique, to give 6-cyano-2,2-dimethyl-7-nitro-2H-benzo[b]pyran (4.00 g) as orange crystals. A small sample was recrystallised from ethyl acetate—60°-80° petroleum ether to yield orange crystals, mp 154°-155° C. nmr (CDCl$_3$) δ 1.51 (s, 6H), 5.89 (d, J=10, 1H), 6.34 (d, J=10, 1H), 7.40 (s, 1H) 7.62 (s, 1H); ir (nujol mull) 2220, 1530, 1330 cm$^{-1}$. Anal. Calcd. for C$_{12}$H$_{10}$N$_2$O$_3$: C, 62.61; H, 4.38; N, 12.17. Found: C, 62.40; H, 4.51; N, 12.04%.

This benzopyran (2.29 g), electrolytic iron powder (1.94 g) and glacial acetic acid (100 ml) were stirred at 100° C. (oil bath temperature) for 1 hour. Dilution with water and extraction into ethyl acetate, washing of the organic phase with water, brine, drying and removal of solvent in vacuo afforded 7-amino-6-cyano-2,2-dimethyl-2H-benzo[b]pyran (1.98 g) as dark orange crystals. A small sample was recrystallised twice from ethyl acetate—60°-80° petroleum ether to give yellow crystals mp 137°-138° C.; nmr (CDCl$_3$) δ 1.39 (s, 6H), 4.20-4.52 (broad, 2H, exch. with D$_2$O), 5.48 (d, J=10, 1H), 6.10 (s, 1H) overlapped with 6.16 (d, J=10, 1H), 6.97 (s, 1H); ir (nujol mull) 3340, 3240, 2220 cm$^{-1}$. Anal. Calcd. for C$_{12}$H$_{12}$N$_2$O; C, 71.98; H, 6.04; N, 13.99. Found: C, 71.31; H, 5.84; N, 13.49%. Mass spectrum: m/e=200.

This benzopyran (1.88 g) was stirred vigorously with acetic anhydride (30 ml) in ethanol (80 ml) at room temperature for 8 hours. The reaction mixture was evaporated in vacuo to afford 7-acetamido-6-cyano-2,2-dimethyl-2H-benzo[b]pyran as a dark orange solid (2.20 g). A small sample was recrystallised twice from ethyl acetate—60°-80° petroleum ether to give yellow crystals mp 136°-137° C.; (CDCl$_3$) δ 1.43 (s, 6H), 2.21 (s, 3H), 5.61 (d, J=10, 1H), 6.20 (d, J=10, 1H), 7.11 (s, 1H), 7.40-7.64 (broad, 1H, exch. with D$_2$O), 7.84 (s, 1H); ir (chloroform solution) 3410, 2200, 1700 cm$^{-1}$. Anal. Calcd for C$_{14}$H$_{14}$N$_2$O$_2$: C, 69.41; H, 5.82; N, 11.56. Found: C, 69.20; H, 5.98; N, 11.53%.

To this benzopyran (2.06 g) dissolved in dimethyl sulphoxide (50 ml) and water (0.18 ml) was added N-bromo-succinimide (1.74 g) with stirring. After 30 minutes the mixture was diluted with water, extracted into ethyl acetate, the organic phase was washed with water, brine, dried and evaporated in vacuo to give 7-acetamido-trans-3-bromo-6-cyano-3,4-dihydro-2,2-dimethyl-2H-benzo[b]pyran-4-ol as an orange solid (2.44 g). Recrystallisation from ethyl acetate—60°-80° petroleum ether gave yellow crystals (1.62 g) mp 191°-192° C.; nmr (CDCl$_3$) 1.40 (s, 3H); 1.60 (s, 3H); 2.21 (s, 3H); 2.68-2.82 (m, H, exch. with D$_2$O); 4.04 (d, J=10, 1H); 4.83 (m, falls to d with D$_2$O, J=10, 1H); 7.43-7.58 (m, exch. with D$_2$O, 1H); 7.71 (s, 1H); 7.89 (s, 1H); ir (nujol mull) 3100-3500, 2225, 1685 cm$^{-1}$. Anal. Calcd. for C$_{14}$H$_{15}$Br N$_2$O$_3$: C, 49.58; H, 4.46; N, 8.26. Found: C, 49.87; H, 4.62; N, 8.19%.

This bromohydrin (1.62 g) and pyrrolidine (0.80 ml) were refluxed in ethanol (50 ml) for 24 hours. The reaction mixture was evaporated in vacuo to afford a brown gum which was dissolved in chloroform, washed with sodium carbonate solution, water, dried and evaporated in vacuo to give a brown foam (1.51 g), which was chromatographed on a silica gel column using ethyl acetate—60°-80° petroleum ether mixtures in a gradient elution technique to afford 7-acetamido-6-cyano-3,4-dihydro-2,2-dimethyl-trans-4-pyrrolidino-2H-benzo[b]pyran-3-ol as a dark yellow solid (0.79 g). A sample was recrystallised from ethyl acetate—60°-80° petroleum ether to give yellow crystals mp 175°-176° C.; nmr (CDCl$_3$) δ 1.22 (s, 3H); 1.50 (s, 3H), 1.72-2.04 (m, 4H), 2.22 (s, 3H); 2.57-3.14 (m, 5H); 3.58 (d, J=10, 1H); 3.95 (d, J=10, 1H); 7.43 (s) overlapped with 7.43 (broad, total of 2H); 7.79 (s, 1H); ir (chloroform solution) 3410, 2200, 1700 cm$^{-1}$. Anal. Calcd. for C$_{18}$H$_{23}$N$_3$O$_3$: C, 65.63; H, 7.04; N, 12.76. Found: C, 64.51; H, 6.87; N, 12.28%. Consistent analysis was not obtained. Mass spectrum: Chemical Ionization, (M+H)$^+$ at m/e 330.

EXAMPLE 6

7-Acetamido-6-carboxamido-3,4-dihydro-2,2-dimethyl-trans-4-piperidino-2H-benzo[b]pyran-3-ol hydrochloride Bromohydrin (1.01 g, as obtained in example 5) and piperidine (0.59 ml) were refluxed in ethanol (75 ml) for 18 hours. The reaction mixture was evaporated in vacuo to afford a gum which was taken up in an ethyl acetate-water mixture, basified with sodium carbonate solution and the organic phase separated from the aqueous, washed with water, brine, dried and evaporated in vacuo to give an orange foam which was subjected to an acid-base extraction (using dilute hydrochloric acid followed by 10% sodium hydroxide solution) to give 7-acetamido-6-carboxamido-3,4-dihydro-2,2-dimethyl-trans-4-piperidino-2H-benzo[b]pyran-3-ol as a brown foam (0.40 g), nmr (DMSOd$_6$) 1.16 (s, 3H), 1.33 (s) overlapped with 1.20-1.66 (m, total of 9H), 2.01 (s, 3H), 2.35-2.82 (m) overlapped with 2.49 (DMSOd$_6$), 3.23-3.50 (m) overlapped with 3.45 (water in DMSOd$_6$), 5.11-5.32 (m, exch. with D$_2$O, 1H), 7.02-8.12 (broad, exch. with D$_2$O, 3H) overlapped with 7.73 (s, 1H), 7.90 (s, 1H), ir (nujol mull) 3000-3500, 1660 cm$^{-1}$, mass spectrum chemical ionization, (M+H)$^+$ at m/e=362. The free base (0.38 g) was dissolved in a minimum volume of ethanol, addition of ethereal HCl produced a yellow precipitate which was recrystallised from ethanol-ether to give the hydrochloride salt as a white powdery monohydrate (0.15 g) mp 210°–213° C. Anal. Calcd. for $C_{19}H_{27}N_3O_4$ HCl. $H_2O$: C, 54.87; H, 7.27; N, 10.10. Found: C, 54.80; H, 7.47; N, 9.82%.

EXAMPLE 7

7-Amino-6-cyano-3,4-dihydro-2,2-dimethyl-trans-4-pyrrolidino-2H-benzo[b]pyran-3-ol dihydrochloride To 4-dimethylaminopyridine (3.91 g) and trifluoroacetic anhydride (4.51 ml) in chloroform (50 ml) was added 7-amino-6-cyano-2,2-dimethyl-2H-benzo[b]pyran (3.18 g, obtained as in Example 5) in chloroform (50 ml) with stirring at room temperature over a period of 10 minutes. The red mixture was stirred under reflux for 2 hours, cooled, washed with water, dried, evaporated to dryness under reduced pressure to give 6-cyano-2,2-dimethyl-7-trifluoroacetylamino-2H-benzo[b]pyran (4.43 g) as a dark orange solid. A small sample was recrystallised from ethyl acetate—60°–80° petroleum ether to give yellow crystals mp 87°–88° C.

nmr (CDCl$_3$) δ 1.48 (s, 6H); 5.70 (d, J=10, 1H); 6.28 (d, J=10, 1H); 7.24 (s, 1H); 7.78 (s, 1H); 8.05–8.51 (broad, exch. with $D_2O$, 1H);

ir (nujol mull) 3280, 2210, 1730 cm$^{-1}$.

Analysis: Calculated for $C_{14}H_{11}N_2O_2F_3$; C, 56.76; H, 3.74; N, 9.46. Found: C, 56.64; H, 3.80; N, 9.32%.

Mass spectrum: m/e =2.96 for M$^+$.

To this benzopyran (4.23 g) and water (0.29 ml) in dimethyl sulphoxide (60 ml) was added freshly crystallised N-bromosuccinimide (2.98 g) with stirring. After 30 minutes the mixture was diluted with water and the resulting emulsion extracted with ethyl acetate. The organic phase was washed with water, brine, then dried and evaporated in vacuo to give crude trans-3-bromo-6-cyano-3,4-dihydro-2,2-dimethyl-7-trifluoroacetyl-amino-2H-benzo[b]pyran-4-ol (5.00 g) as a orange gum. Two recrystallisations from ethyl acetate—60°–80° petroleum ether gave a pale yellow solid (1.75 g) mp 183°–184° C.

nmr (CDCl$_3$) δ 1.46 (s, 3H); 1.66 (s, 3H); 2.56–3.00 (broad, exch. with $D_2O$, 1H); 4.08 (d, J=10, 1H); 4.87 (d, J=10, 1H); 7.86 (s, 2H); 8.00–8.67 (broad, exch. with $d_2O$, 1H).

ir (nujol mull) 3575, 3400, 2225, 1730 cm$^{-1}$.

Analysis: Calculated for $C_{14}H_{12}N_2O_3BrF_3$: C, 42.77; H, 3.08; N, 7.13. Found: C, 42.59, H, 3.19; N, 7.03%.

Mass Spectrum: m/e=391 for M$^+$.

This bromohydrin (1.55 g) and pyrrolidine (15 ml) were refluxed together for 30 minutes, cooled, diluted with water, extracted with ethyl acetate and washed with water. The organic layer was extracted with 5NHCl, basified with 10% NaOH solution and extracted into ethyl acetate, washed with water, dried and evaporated to dryness in vacuo to give 7-amino-6-cyano-3,4-dihydro-2,2-dimethyl-trans-4-pyrrolidino-2H-benzo[b]pyran-3-ol (0.64 g) as an orange foam. A small sample crystallised from ethyl acetate—60–80° petroleum ether had mp 158°–160° C.

nmr (CDCl$_3$) δ 1.23 (s, 3H); 1.49 (s, 3H); 1.65–2.13 (m, 4H); 2.62–3.15 (m, 5H falls to 4H with $D_2O$); 3.50 (d, J=10, 1H); 3.85 (d, J=10, 1H); 4.28 (broad s, exch. with $D_2O$, 2H); 6.16 (s, 1H); 7.29 (s, 1H).

ir (chloroform solution) 3500, 3400, 2200 cm$^{-1}$.

The crude free base (0.51 g) was dissolved in a minimum volume of ethanol and addition of etheral-HCl produced a light brown precipitate which was recrystallised twice from ethanol-ether to give the hydrochloride salt (0.33 g) as a light brown hydrated solid of mp 173°–174° C.

Analysis: Calculated for $C_{16}H_{21}N_3O_2.HCl.\frac{3}{4}H_2O$; C, 57.14; H, 6.74; N, 12.49; Cl, 10.54. Found: C, 56.94; H, 7.12; N, 11.94; Cl, 10.51%.

Mass spectrum: chemical ionization: m/e=288 for $[M+H-HCl-\frac{3}{4}H_2O]^+$.

The structures of the compounds prepared in the above Examples are as follows:

EXAMPLE 1

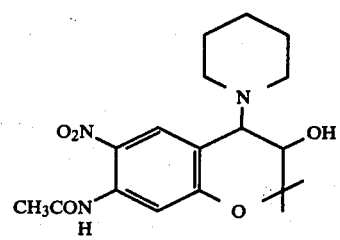

EXAMPLE 2

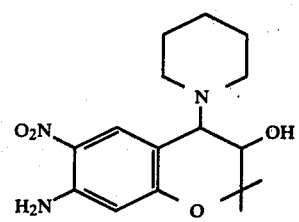

EXAMPLE 3

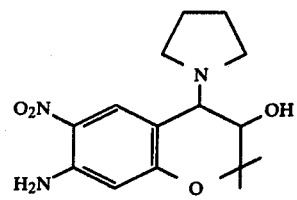

EXAMPLE 4

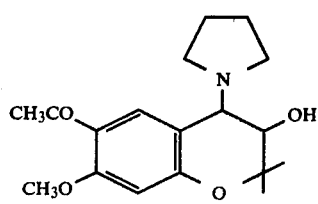

EXAMPLE 5

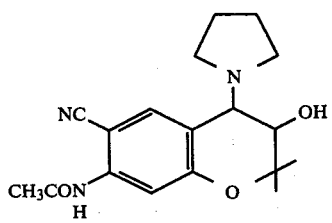

EXAMPLE 6

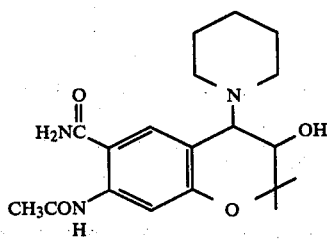

EXAMPLE 7

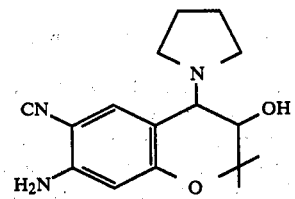

DEMONSTRATION OF EFFECTIVENESS

Biological Data

Systolic blood pressures were recorded by a modification of the tail cuff method described by J. M. Claxton, M. G. Palfreyman, R. H. Poyser and R. L. Whiting, European Journal of Pharmacology, 37, 179 (1976). An oscilloscope of W+W BP recorder, model 8002, was used to display pulses. Prior to all measurements rats were placed in a heated environment (33.5°±0.5° C.) before transfer to a restraining cage. Each determination of blood pressure was the mean of at least 6 readings. Spontaneously hypertensive rats (aged 12–18 weeks) with systolic blood pressures >170 mmHg were considered hypertensive.

| Compound of Example No. | Time Post dose (hrs) | % change in Systolic Blood pressure | % change in heart rate |
|---|---|---|---|
| 1 | Initial values | 199 ± 7 | 471 ± 10 |
| 10 mg/kg | 1 | −46* | +15* |
| p.o. | 2 | −* | −* |
| 5 rats | 4 | −49 ± 1 | +9 ± 4 |
| | 6 | −51 ± 2 | +2 ± 4 |
| | 24 | −6 ± 1 | −6 ± 1 |
| 2 | Initial Values | 199 ± 4 | 426 ± 24 |
| 0.03 mg/kg | 1 | −28 ± 3 | +3 ± 7 |
| p.o. | 2 | −37 ± 2 | −4 ± 5 |
| 6 rats | 4 | −27 ± 3 | −2 ± 7 |
| | 6 | −27 ± 3 | −7 ± 10 |

-continued

| Compound of Example No. | Time Post dose (hrs) | % change in Systolic Blood pressure | % change in heart rate |
|---|---|---|---|
| 5 | 24 | +4 ± 2 | −1 ± 4 |

*At 1 hour only 2 rats had measurable pulses. At 2 hours no rats had measurable pulses.

| Compound of Example No. | Time Post dose (hrs) | % change in Systolic Blood pressure | % change in heart rate |
|---|---|---|---|
| (3) | Initial value | 209 ± 9 | 441 ± 14 |
| | 1 | −22 ± 5 | 4 ± 11 |
| 0.03 mg/kg | 2 | −10 ± 4 | −3 ± 12 |
| p.o. | 4 | −6 ± 4 | −1 ± 9 |
| | 6 | −4 ± 3 | −2 ± 9 |
| 6 rats | 24 | −3 ± 4 | +2 ± 11 |
| (4) | Initial value | 224 ± 5 | 459 ± 11 |
| | 1 | −13 ± 2 | 0 ± 10 |
| 3 mg/kg | 2* | −24 | +1 |
| p.o. | 4 | −23 ± 3 | −6 ± 6 |
| | 6 | −18 ± 3 | −2 ± 6 |
| 6 rats | 24 | −8 ± 3 | −1 ± 5 |

At 2 hours pulses were only detectable in 2 rats.

| | | | |
|---|---|---|---|
| (5) | Initial values | 224 ± 5 | 487 ± 5 |
| 0.3 mg/kg | | | |
| p.o. | 1 | −58 ± 2 | 0 ± 2 |
| | 2 | −64 ± 1* | 0 ± 4 |
| 6 rats | 4 | −61 ± 4* | 0 ± 3 |
| | 6 | −58 ± 2* | +1 ± 2 |
| | 24 | −6 ± 4 | +9 ± 1 |

*At 2 and 4 hours only 3 rats had measurable pulses. At 6 hours only 4 rats had measurable pulses.

| | | | |
|---|---|---|---|
| (6) | Initial values | 217 ± 4 | 458 ± 9 |
| 3 mg/kg | | | |
| p.o. | 1 | −10 ± 3 | −3 ± 7 |
| | 2 | −10 ± 3 | −7 ± 8 |
| 6 rats | 4 | −36 ± 2 | −5 ± 7 |
| | 6 | −31 ± 2 | −3 ± 7 |
| | 24 | −4 ± 2 | −2 ± 3 |
| (7) | Initial values | 223 ± 3 | 422 ± 14 |
| | 1 | −24 ± 5 | +22 ± 6 |
| 0.1 mg/kg | 2 | −16 ± 4 | +8 ± 5 |
| 6 rats | 4 | −19 ± 4 | +1 ± 2 |
| | 6 | −14 ± 5 | +2 ± 4 |
| | 24 | +2 ± 3 | −3 ± 4 |

TOXICITY

No toxic effects were observed in these tests.

We claim:

1. A compound of the formula:

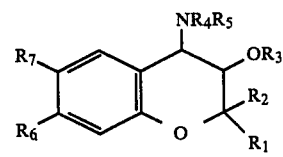

or a pharmaceutically acceptable salt or ester thereof, wherein $R_1$ is hydrogen or lower alkyl;
$R_2$ is hydrogen or lower alkyl;
$R_3$ is hydrogen or lower alkyl;
$R_4$ is hydrogen or lower alkyl;
$R_5$ is lower alkyl or alkyl of 3 to 5 carbon atoms terminally substituted by chlorine;
or $R_4$ and $R_5$ are joined so that together with the nitrogen atom to which they are attached they form a 6- or 7-membered saturated heterocyclic ring containing said nitrogen atom as the sole hetero atom or a 5- membered saturated heterocyclic ring optionally containing an oxygen or sulphur atom as an additional hetero atom;

$R_6$ is amino, carboxylic acylamino of up to 3 carbon atoms, alkylamino of up to 3 carbon atoms, or dialkylamino of up to 3 carbon atoms in each alkyl moiety;

$R_7$ is nitro or cyano;

and the $NR_4R_5$ and $OR_3$ groups are trans.

2. A compound according to claim 1 of the formula

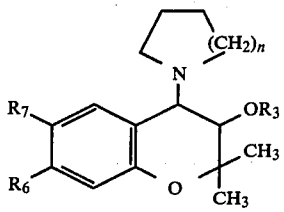

or a pharmaceutically acceptable salt or ester thereof wherein $R_3$, $R_6$ and $R_7$ are as defined in claim 1 and n is 1 or 2, the cyclic amino and $OR_3$ groups being trans.

3. A compound according to claim 2 of the formula:

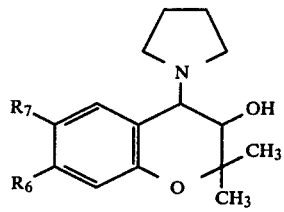

4. A compound according to claim 2 of the formula:

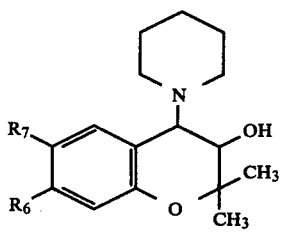

5. A compound according to claim 1, wherein $R_4$ and $R_5$ are joined so that together with the nitrogen atom to which they are attached they form pyrrolidino or piperidino.

6. A compound according to claim 3 wherein $R_6$ is amino.

7. A compound according to claim 1 wherein $R_7$ is nitro.

8. 7-Amino-6-cyano-3,4-dihydro-2,2-dimethyl-trans-4-pyrrolidino-2H-benzo[b]pyran-3-ol.

9. An anti-hypertensive composition comprising an anti-hypertensively effective amount of a compound according to claim 1 in combination with a pharmaceutically acceptable carrier.

10. A method of effecting an anti-hypertensive response in a human or other animal which comprises administering thereto an effective amount of a compound according to claim 1.

* * * * *